(12) United States Patent
Clemens et al.

(10) Patent No.: US 12,070,394 B2
(45) Date of Patent: Aug. 27, 2024

(54) INTERVERTEBRAL SPACER FOR TLIF IMPLANT PROCEDURE

(71) Applicant: Nexxt Spine, LLC, Noblesville, IN (US)

(72) Inventors: Austin Clemens, Indianapolis, IN (US); Chad Birchler, Noblesville, IN (US); Anthony Woods, Noblesville, IN (US); Andrew Elsbury, McCordsville, IN (US); Caleb Morin, Greenfield, IN (US)

(73) Assignee: Nexxt Spine, LLC, Noblesville, IN (US)

( * ) Notice: Subject to any disclaimer, the term of this patent is extended or adjusted under 35 U.S.C. 154(b) by 619 days.

(21) Appl. No.: 17/410,548

(22) Filed: Aug. 24, 2021

(65) Prior Publication Data
US 2021/0378838 A1 Dec. 9, 2021

Related U.S. Application Data

(62) Division of application No. 16/930,605, filed on Jul. 16, 2020, now Pat. No. 11,344,431.

(60) Provisional application No. 62/881,581, filed on Aug. 1, 2019.

(51) Int. Cl.
*A61F 2/44* (2006.01)
*A61F 2/30* (2006.01)

(52) U.S. Cl.
CPC .......... *A61F 2/4455* (2013.01); *A61F 2/4425* (2013.01); *A61F 2002/30332* (2013.01); *A61F 2002/30561* (2013.01)

(58) Field of Classification Search
CPC .................. A61F 2/4455; A61F 2/4425; A61F 2002/30332; A61F 2002/30561
See application file for complete search history.

(56) References Cited

U.S. PATENT DOCUMENTS

| 8,147,554 | B2 | 4/2012 | Hansell et al. |
| 8,545,566 | B2 | 10/2013 | Niemiec et al. |
| 2018/0303624 | A1* | 10/2018 | Shoshtaev ............. A61F 2/4465 |
| 2019/0105172 | A1 | 4/2019 | Sournac et al. |

* cited by examiner

*Primary Examiner* — Nirvana Deonauth
(74) *Attorney, Agent, or Firm* — Maginot, Moore & Beck, LLP

(57) ABSTRACT

An intervertebral spacer is disclosed having a main body and an articulating component that is pivotally mounted within an opening of the main body. The intervertebral spacer is designed to be manufactured using an additive manufacturing process without the use of any frangible support material between a main body of the intervertebral spacer and an articulating component of the intervertebral spacer. To this end, an article of manufacture is provided in which supports are formed prior to forming intervertebral spacer. The supports are configured to support the main body and the articulating component such that they can be separately, but simultaneously manufactured using an additive manufacturing process atop the supports, without the need for any frangible support material therebetween.

13 Claims, 13 Drawing Sheets

SECTION G-G

SECTION F-F

INTERVERTEBRAL SPACER FOR TLIF IMPLANT PROCEDURE

This application is a divisional of co-pending application Ser. No. 16/930,605, filed on Jul. 16, 2020, which claims the benefit of priority of U.S. provisional application Ser. No. 62/881,581, filed on Aug. 1, 2019, the disclosures of which are herein incorporated by reference in their entirety.

FIELD

The device and method disclosed in this document relates to intervertebral implants or spacers for fusing vertebral bodies and, more particularly, to an intervertebral spacer configured and dimensioned to be implanted transforaminally.

BACKGROUND

Unless otherwise indicated herein, the materials described in this section are not admitted to be prior art by inclusion in this section.

In humans, the normal spine has seven cervical, twelve thoracic and five lumbar segments. The bony vertebral bodies of the spine are separated by intervertebral discs, which act as joints but allow known degrees of flexion, extension, lateral bending, and axial rotation. The typical vertebra has a thick anterior bone mass called the vertebral body, with a neural (vertebral) arch that arises from the posterior surface of the vertebral body. The central portions of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the posterior side of spinal cord is known as the lamina. Projecting from the posterior region of the neural arch is the spinous process.

The intervertebral disc primarily serves as a mechanical cushion permitting controlled motion between vertebral segments of the axial skeleton. A normal and healthy intervertebral disc is a unique, mixed structure, comprised of three component tissues: the nucleus pulpous ("nucleus"), the annulus fibrosus ("annulus"), and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc.

The spinal disc and/or vertebral bodies may be displaced or damaged due to trauma, disease, degenerative defects, or wear over an extended period of time. One result of this displacement or damage to a spinal disc or vertebral body may be chronic back pain.

A disc herniation occurs when the annulus fibers are weakened or torn and the inner tissue of the nucleus becomes permanently bulged, distended, or extruded out of its normal, internal annulus confines. Alternatively, with disc degeneration, the nucleus loses its water-binding ability and deflates, as though the air had been let out of a tire. Subsequently, the height of the nucleus decreases causing the annulus to buckle in areas where the laminated plies are loosely bonded. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the disc is removed along with all or part of at least one neighboring vertebrae and an implant is introduced into the resulting space that promotes fusion of the remaining bony anatomy. The implant or spacer, which can be in the form of a cage, fills the space left by the removed disc and bony anatomy and must be sufficiently strong to support the spine under a wide range of loading conditions. The spacer should also be configured so that it is likely to remain in place once it has been positioned in the spine by the surgeon. Optimally, the spacer is designed to promote bony ingrowth through the spacer, which a can be accomplished by the physical structure of the spacer, as well as forming the spacer of a biocompatible material that at least accommodates, if not promotes, bony tissue ingrowth.

Instrumentation and specialized tools for insertion of an intervertebral spacer is yet another design parameter to consider when designing a spacer. Spinal fusion procedures can present several challenges because of the small clearances around the spacer when it is being inserted into position. For instance, the instrumentation used may securely grip the spacer on opposing sides or surfaces. Thus, the clearance required in order to insert such a spacer must be greater than the spacer itself in order to accommodate the instrumentation. For this reason, distraction of the treated area typically is greater than the spacer itself. Similarly, when the gripping tools used to manipulate and insert the spacer are on the sides of the spacer, additional clearance typically is needed in order to accommodate the added width of the insertion tool blades. Such increases in height or width of the profile of the spacer when coupled or in communication with instrumentation means that additional space is needed in order to insert the spacer. In some circumstances, providing for this additional clearance space can be difficult to achieve.

It is thus well known to immobilize two vertebrae relative to one another using an intervertebral implant made from a rigid material, forming a cage that delimits a housing that is configured to receive one or several bone grafts and/or spongy bone chips. Some intervertebral cages or spacers are implanted through a posterior approach called "PLIF" (acronym for Posterior Lumbar Interbody Fusion), others through an anterior approach "ALIF" (Anterior Lumbar Interbody Fusion), and still others through a transforaminal approach or "TLIF" (Transforaminal Lumbar Interbody Fusion).

FIGS. 1A-1D depict an exemplary transforaminal approach for implanting an intervertebral spacer 10. In this approach, the spacer 10 has a curved contour that facilitates its introduction into the intervertebral space using an insertion tool T. The insertion tool T is engaged at an interface I to an articulating or rotating element 12 of the spacer 10. The insertion tool T also includes a stabilizer component S that engages the end of the spacer 10 to hold the insertion tool T in a fixed relationship to the spacer 10. Thus, as can be seen in FIG. 1A, in an initial step, the insertion tool T is engaged to the spacer 10 with the stabilizer component S such that the spacer 10 is, in essence, a rigid extension of the insertion tool T. The spacer 10 is introduced to a desired positioning or depth between adjacent vertebral bodies using a transforaminal approach. With the spacer 10 initially positioned, the stabilizing component S is retracted, as shown in FIG. 1B, with the interface I still engaged to the spacer 10. With the stabilizer component disengaged from the spacer 10, the spacer 10 is free to pivot within the intervertebral space as the insertion tool T is advanced into the intervertebral space, as shown in FIGS. 1C-1D. Once impacted to the desired position, such as adjacent the epiphyseal ring, the interface I of the insertion tool T is released from the spacer 10, leaving the spacer 10 implanted within the patient.

SUMMARY

An article of manufacture is disclosed in one feature of the present disclosure that comprises an intervertebral spacer that includes a main body having a distal end and a proximal end that are connected by side walls that are spaced apart from one another so as to define an interior cavity therebetween, the proximal end having a first proximal end wall and a second proximal end wall, a proximal end opening being defined between the first proximal end wall and the second proximal end wall; and an articulating component pivotally mounted within the proximal end opening and configured to interconnect with a tool for inserting the intervertebral spacer. The article of manufacture further comprises a plurality of support structures connected to the intervertebral spacer including at least one first support structure configured to support the main body of the intervertebral spacer during manufacture and at least one second support structure configured to support the articulating component of the intervertebral spacer during manufacture, the plurality of support structures being removable from the intervertebral spacer after manufacture.

An intervertebral spacer is disclosed in one feature of the present disclosure that comprises a main body having a distal end and a proximal end that are connected by side walls that are spaced apart from one another so as to define an interior cavity therebetween, the proximal end having a first proximal end wall and a second proximal end wall, a proximal end opening being defined between the first proximal end wall and the second proximal end wall. The intervertebral spacer further comprises an articulating component having an elongated shape with a first end that is pivotally mounted within the proximal end opening and a second end that is configured to interconnect with a tool for inserting the intervertebral spacer. One of (i) an interior of the proximal end opening and (ii) the first end of the articulating component includes a protrusion coinciding with a pivotal axis of the articulating component and another one of (i) the interior of the proximal end opening and (ii) the first end of the articulating component includes a recess coinciding with the pivotal axis of the articulating component. The protrusion is configured to be received within the recess to enable a pivoting motion of the articulating component about the pivotal axis.

A method for manufacturing intervertebral spacer is disclosed in one feature of the present disclosure that comprises manufacturing, using an additive manufacturing processing, atop a surface, at least one first support structure configured to support a main body of the intervertebral spacer during manufacture and at least one second support structure configured to support an articulating component of an intervertebral spacer during manufacture. The method further comprises manufacturing, using the additive manufacturing processing, the main body atop the at least one first support structure, the main body having a distal end and a proximal end that are connected by side walls that are spaced apart from one another so as to define an interior cavity therebetween, the proximal end having a first proximal end wall and a second proximal end wall, a proximal end opening being defined between the first proximal end wall and the second proximal end wall. The method further comprises manufacturing, using the additive manufacturing processing, the articulating component atop the at least one second support structure without any material interconnecting the main body and the articulating component, the articulating component being pivotally mounted within the proximal end opening and configured to interconnect with a tool for inserting the intervertebral spacer. The method further comprises removing, after the manufacture of the main body and the articulating component, the at least one first support structure from the main body and the at least one second support structure from the articulating component.

BRIEF DESCRIPTION OF THE DRAWINGS

The foregoing aspects and other features of the arrangement, intervertebral spacer, and method are explained in the following description, taken in connection with the accompanying drawings.

DETAILED DESCRIPTION

Figure 1A:
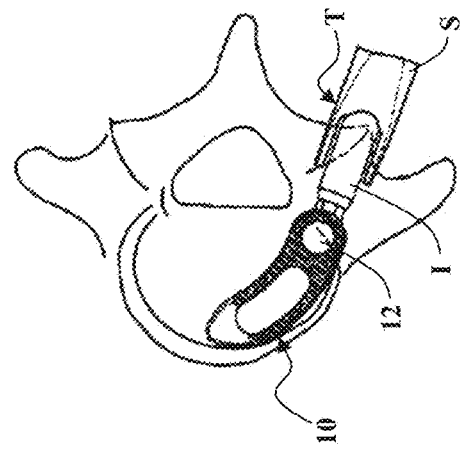
FIGS. 1A-1D depict of an intervertebral spacer being introduced into an intervertebral space using a transforaminal approach.
Figure 1B:
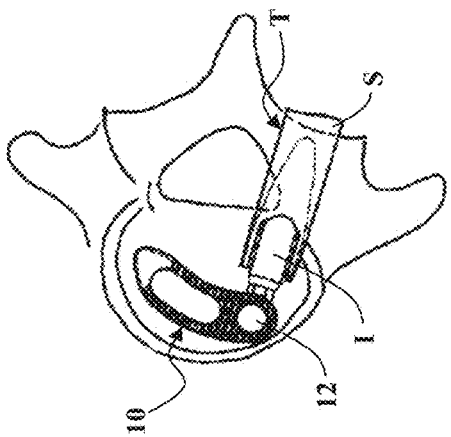
Figure 1C:
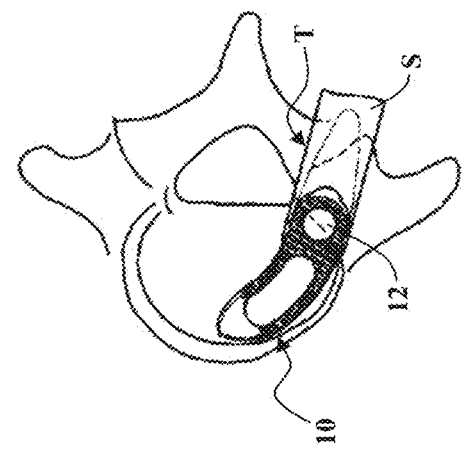
Figure 1D:
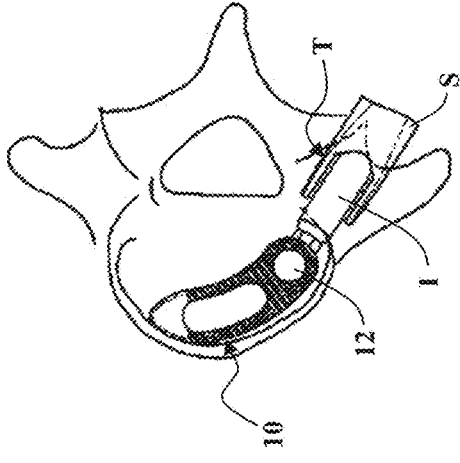

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

Figure 2A:
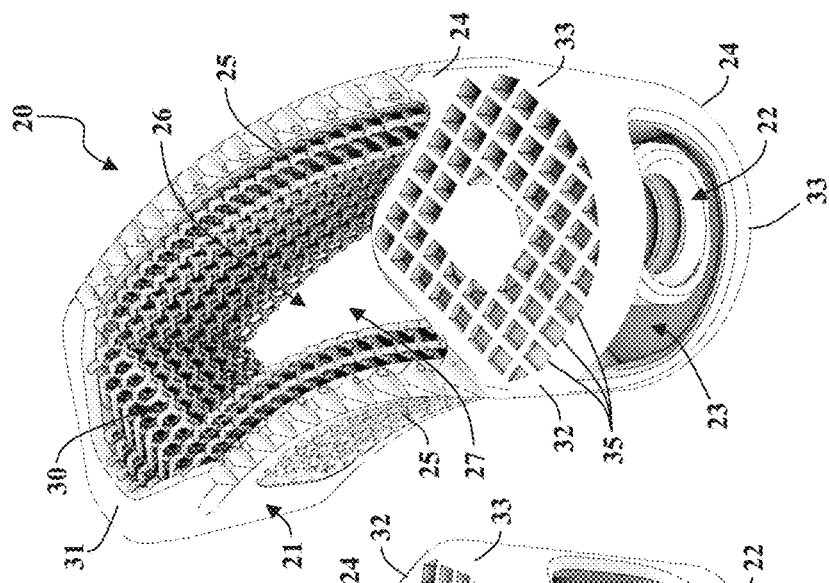
FIGS. 2A-2C are perspective views of an intervertebral spacer adapted for introduction using the transforaminal approach.
Figure 2B:
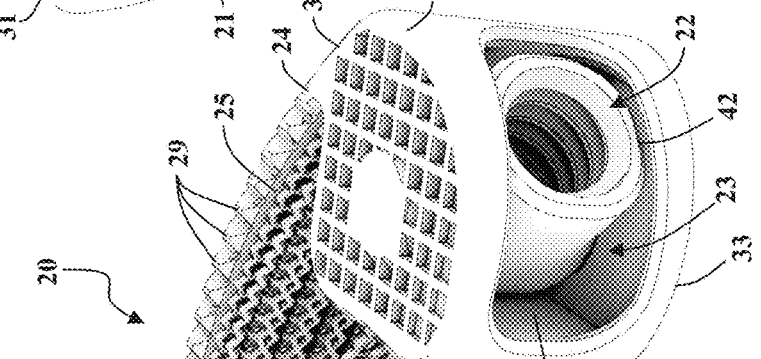
Figure 2C:
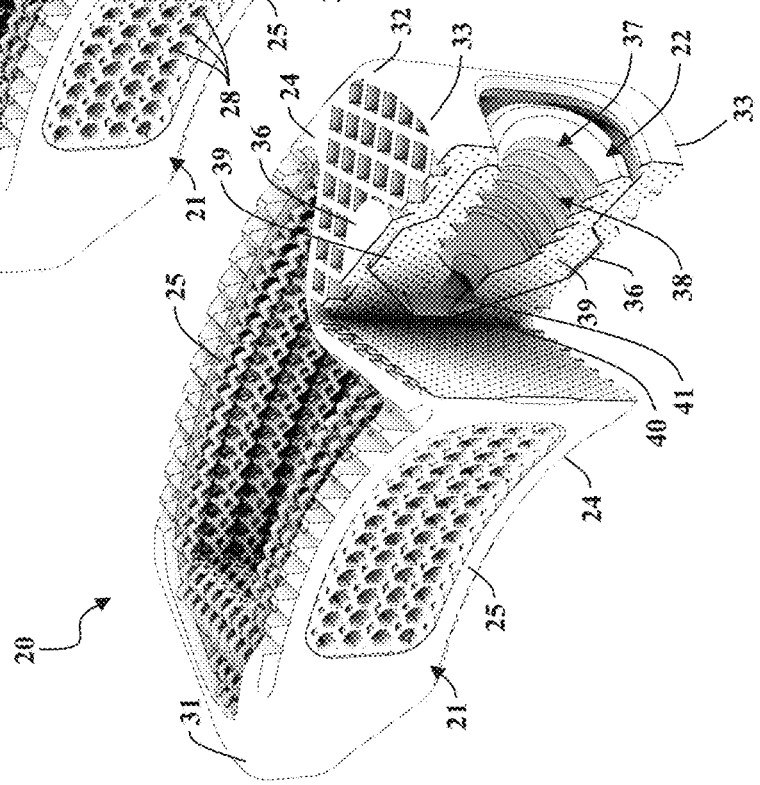

FIGS. 2A-2C are perspective views of an intervertebral spacer 20 according to the disclosure which is adapted for introduction using the transforaminal approach, for example as depicted in FIGS. 1A-1D. The spacer 20 is comprised of a main body 21 and an articulating component 22 (which may also be referred to as an "articulating pin") that is pivotally mounted within an opening 23 defined in one end of the main body 21. As will be described in further detail herein, in at least some embodiments the spacer 20 is formed using a digital additive manufacturing process, such as three-dimensional object printing (also referred to as simply "3D printing"). Moreover, the spacer 20 is advantageously designed to be manufactured without the use of any frangible support material between the main body 21 and the articulating component 22, as is required with other designs using a digital additive manufacturing process.

The main body 21 has a hollow cage structure and is formed primarily by upper and lower walls 24 and by opposite side walls 25, which together define an interior cavity 26 of the main body 21. The upper and lower walls 24 are generally planar and shaped to exhibit a large curvature that corresponds to prepared endplates of adjacent vertebrae being treated with the spacer 20. The opposite side walls 25 are spaced from one another and connected to edges of the upper and lower walls 24 so as to define an interior cavity 26 between the opposite side walls 25 and the upper and lower walls 24. Thus, it should be appreciated that the opposite side walls 25 have a non-planar curved shape configured to match the contour of the edges of the upper and lower walls 24, which may, for example, emulate the curvature of the epiphyseal ring to facilitate advancement of the spacer 20 into the intervertebral space. Moreover, it should be appreciated that the upper and lower walls 24 are defined in part by the upper and lower edges of the opposite side walls 25. Likewise, the opposite side walls 25 are defined in part by the edges of the upper and lower walls 24.

At least some of the upper and lower walls 24 and the opposite side walls 25 are configured to define large openings 27 that make the interior cavity 26 accessible from an exterior of the spacer 20. In the illustrated embodiment, only the upper and lower walls 24 define large through openings 27. However, in alternative embodiments, only the opposite side walls 25 define large through openings 27 or all four of the upper and lower walls 24 and the opposite side walls 25 define large through openings 27. In this way, the interior cavity 26 of the main body 21 is configured to receive bone growth material, such as morcellized bone, bone morphogenic protein (BMP), or other compositions known to promote bone growth and integration into the adjacent vertebral bodies.

In embodiments in which one or more of the side walls 25 or the upper and lower walls 24 do not define large openings 27, some of the side walls 25 or the upper and lower walls 24 may instead be provided with a plurality of smaller openings or apertures 28 passing through the structure of the respective wall and in communication with the interior cavity 26. Particularly, in the illustrated embodiment, the upper and lower walls 24 define large through openings 27, whereas the side walls 25 define pluralities of smaller openings 28. In alternative embodiments, the upper and lower walls 24 define pluralities of smaller openings 28, whereas the side walls 25 define large through openings 27. The smaller openings 28 can have a variety of shapes, including circular or hexagonal, and may extend continuously through the respective side wall 25 or respective upper or lower wall 24. In one embodiment, the respective side wall 25 or respective upper or lower wall 24 can be configured so that the smaller openings 28 define a honeycomb pattern. In some embodiments, the smaller openings 28 are defined by a three-dimensional lattice or mesh structure 30 that forms at least part of the respective side wall 25 or respective upper or lower wall 24. The smaller openings 28 and/or the three-dimensional lattice/mesh structures 30 are configured to accept bone growth stimulating compositions there through to permit bone growth through the respective side wall 25 or respective upper or lower wall 24.

In some embodiments, the upper and lower walls 24 are provided with surface features 29 that are configured to engage the prepared surfaces of the adjacent vertebral bodies. Particularly, in one exemplary embodiment, the surface features 29 are in the form of pyramidal protrusions or teeth that are adapted to penetrate or otherwise engage with the prepared endplates of the adjacent vertebrae being treated with the space 20.

The main body 21 further includes a distal end portion 31 having a blunt-tipped shape, a bullet shape, or other shape configured to facilitate introduction of the spacer 20 into the intervertebral space. In some embodiments, the distal end portion 31 is formed as a joining or connection of the distal ends of each of the upper and lower walls 24 and the opposite side walls 25 to form a blunt tipped pyramidal shape. In some embodiments, the distal end portion 31 has an at least partially hollow structure. In some embodiments, the hollow structure of the distal end portion 31 may be partially or completely filled with a three-dimensional lattice or mesh structure 30, similar to that which defines the smaller openings 28 of side walls 25 or the upper and lower walls 24.

In some embodiments, the distal end portion 31 may incorporate the surface features 29 on one or more of its outer surfaces to further enhance the grip between the spacer 20 and the vertebral bodies. Likewise, in some embodiments, the distal end portion 31 may incorporate the smaller openings 28 to facilitate further bone growth.

The main body 21 further comprises a proximal end portion 32 that is adapted to be engaged by an insertion tool T to perform the TLIF implant procedure described above. In particular, the proximal end portion 32 includes upper and lower walls 33 and an inner wall 34 that define the opening 23 within which the articulating component 22 is mounted. The upper and lower walls 33 form the proximal end portion of the upper and lower walls 24. In one embodiment, the upper and lower walls 33 include small openings 35, which are similar to the smaller openings 28. The inner wall 34 is connected between inner edges of each of the upper and lower walls 33 so as to provide a structural separation between the opening 23 and the interior cavity 26 of main body 21. The upper and lower walls 33 further include a central boss 36 that amounts to an indentation in the thickness of the upper and lower walls 33, as best shown in FIG. 2C. The central bosses or indentations 36 serve as a pivot mount for the articulating component 22 mounted within the opening 23 between the upper and lower walls 33.

The articulating component 22 has an elongated shape that defines a central bore 37 that can incorporate threads 38 for engaging the interface component I of the insertion tool T described above. The articulating component 22 is thus generally cylindrical in shape so that it can pivot freely within the opening 23 of the main body 21. The cylindrical body of the articulating component 22 includes an enlarged end having protrusions 39 that are configured to be seated within the indentations 36 defined in the upper and lower walls 33 of the proximal end portion 32. The distal end of the cylindrical body of the articulating component 22 is configured to receive the interface component I of the insertion tool T. In one embodiment, the enlarged end of the articulating component 22 terminates in a truncated nose 40 with a central bore 41 extending from the threaded bore 37.

It should be appreciated that the interface between the indentations 36 and the protrusions 39 of the articulating component 22 operates as a pivot axis for pivoting of the component form side-to-side between the upper and lower walls 33 of the proximal end portion 32. This articulating movement allows the spacer 20 to be manipulated as necessary for introduction using the transforaminal approach. In one aspect, the articulating component 22 includes flattened sides 42, as shown in FIG. 2B rather than a fully cylindrical body, to reduce the vertical profile of the articulating component 22 while retaining sufficient material to define the threaded bore 37.

In order for the articulating component to be free to pivot within the proximal end portion 30, clearance between the articulating component 22 and the main body 21 of the spacer 20 is necessary. Thus, in accordance with one aspect of the present disclosure, the complete insert 20 is manufactured using an additive manufacturing process, such as a 3D printing, with a uniform gap defined between the articulating component 22 and the body 21. However, in a conventional additive manufacturing process in which the spacer 20 is formed on its side as illustrated, a frangible support structure needs to be provided between the two components. Particularly, for explanatory purposes only, a conventional additive manufacturing process might form the spacer on its side and utilize a frangible bridge to support the articulating component 22 during the additive manufacturing process. The frangible bridge would, for example, comprise a thin strip of material between an exterior surface of the articulating component 22 and the interior surface of the opening 23 in the main body 21. After manufacture, this thin strip of material would be broken by forced movement of the articulating component 22 relative to the main body 21, or be otherwise removed from the spacer 20. However, this technique has the disadvantage of leaving small material remnants of frangible bridge situated between the articulating component 22 and the main body 21 that may inhibit smooth pivotal movement of the articulating component 22 with respect to the main body 21.

Figure 3A:
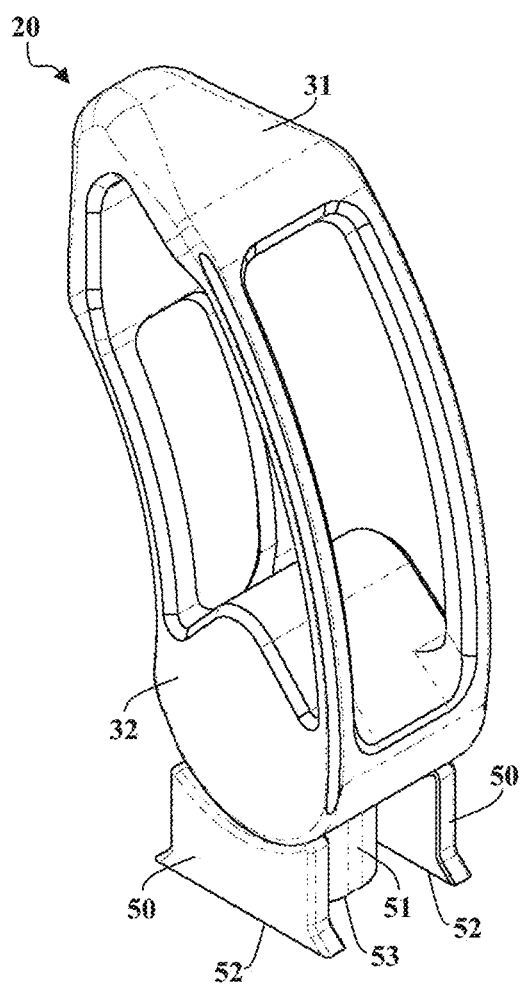
FIGS. 3A-3C are perspective views of the intervertebral spacer having removable supports adapted for additive manufacture of the intervertebral spacer.
Figure 3B:
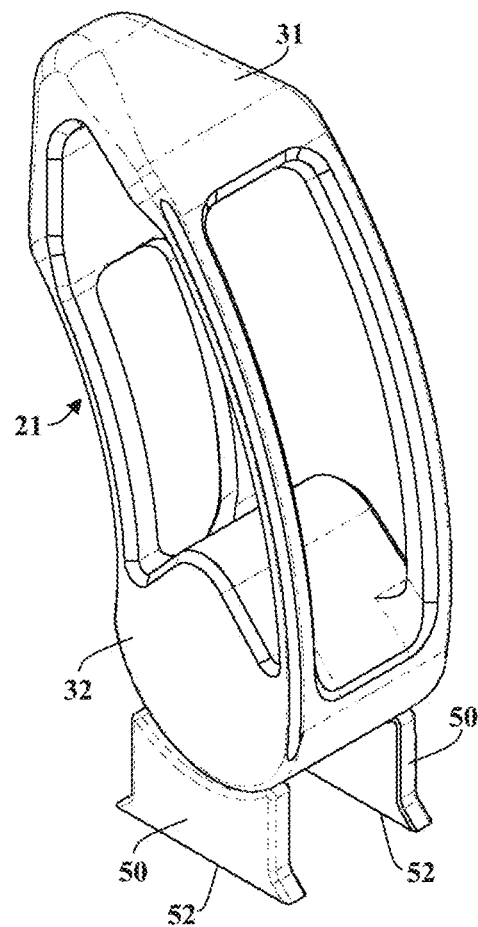
Figure 3C:
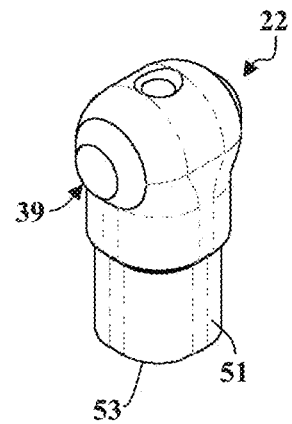

With reference to FIGS. 3A-3C, the intervertebral spacer 20 of the present disclosure is advantageously designed to be manufactured without the use of any frangible support material between the main body 21 and the articulating component 22, as is required in a conventional additive manufacturing process. Instead, the spacer 20 is produced in an additive manufacturing process in which the main body 21 and the articulating component 22 are separately supported during manufacture. Particularly, as shown in FIG. 3A, the spacer 20 further includes support structures 50 and 51 that extend from the main body 21 and the articulating component 22, respectively. The support structures 50 and 51 are advantageously separate from one another and no frangible support material is used that interconnects the main body 21 with the articulating component 22. It should be appreciated that the support structures 50 and 51 may a wide variety of forms include any number of individual elements. For example, in one embodiment, the support structures 50 include four leg structures rather than two wall structures. Similarly, in one embodiment, the support structure 51 includes two flat wall structures, rather than a rounded wall structure.

Figure 4C:
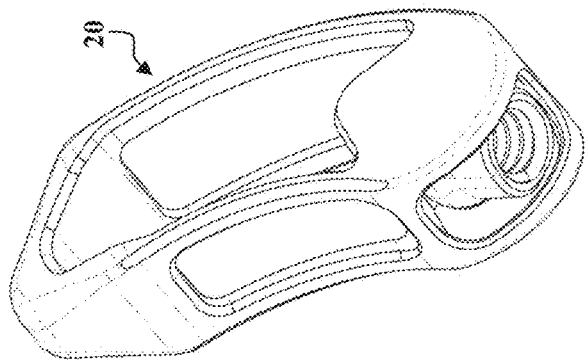
FIGS. 4A-4D are perspective views of the intervertebral spacer of FIGS. 3A-3C illustrating removal of the supports after manufacture.
Figure 4B:
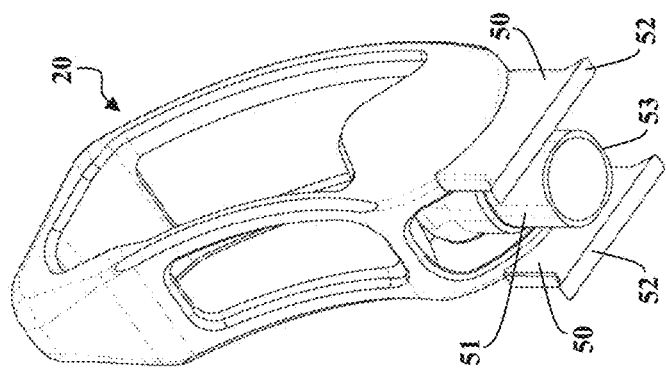
Figure 4D:
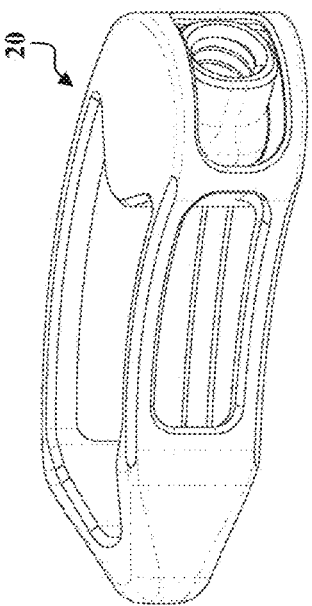
Figure 4A:
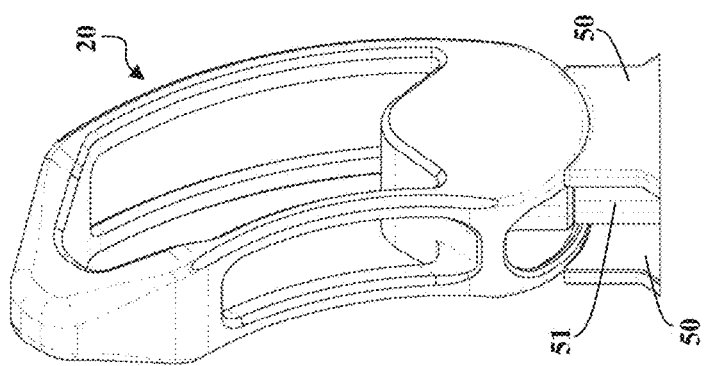

FIG. 3B illustrates the main body 21 without the articulating component 22 mounted therein. As can be seen, support walls 50 extend proximally from the proximal end portion 32 of the main body 21 and are generally planar and contiguous with the upper and lower walls 33 of the proximal end portion 32. Likewise, FIG. 3C illustrates the articulating component 22 separated from the main body 21. As can be seen, a support 51 extends proximally from the end of the threaded bore 37 and generally follows the cylindrical or flattened cylindrical contour of the articulating component 22. FIGS. 4A-4B are additional perspective views of the intervertebral spacer 20 support structures 50 and 51, showing the relative orientations of the support structures.

The support structures 50 and 51 are configured to support the spacer 20 when it rests on a horizontal surface in a vertical orientation. To this end, the support structures 50 and 51 have flat ends 52 and 53, respectively, best seen in FIG. 4B, which are opposite the ends that connect to the main body 21 or articulating component 22, respectively, and are configured to facilitate stable resting of the spacer 20 on the horizontal surface in the vertical orientation. As used herein, the term "vertical orientation" used with respect to the intervertebral spacer 20 refers to an orientation in which the opening 23 of proximal end portion 32 of the main body 21 faces in the direction of gravity and/or faces the horizontal surface, such that supports 50 and 51, extending from the proximal end portion 32 of the main body 21 and from the articulating component 22 may simultaneously rest on the horizontal surface.

The supports 50 and 51 enable the main body 21 and the articulating component 22 to be manufactured together in the vertical orientation using a digital additive manufacturing process, such as 3D printing, without the need for any frangible support material that interconnects the main body 21 with the articulating component 22. In particular, in the vertical orientation, the main body 21 and the articulating component 22 can be printed simultaneously with the articulating component 22 already positioned within the opening 23 of the main body 21, but without contact or connection between the main body 21 and the articulating component 22. It can be appreciated that processes such as 3D printing can very accurately lay down layers of material with accurately sized vertically oriented gaps between the material so that the protrusions 39 of the articulating component 22 can be very near, but not touching, the indentations 36 in the main body 21. In this way, the articulating component 22 reliably provides a smooth pivot motion that is free from undesirable material remnants of a frangible bridge. After manufacture, the supports 50 and 51 are removed, as shown in FIGS. 4C-4D.

Figure 5A:
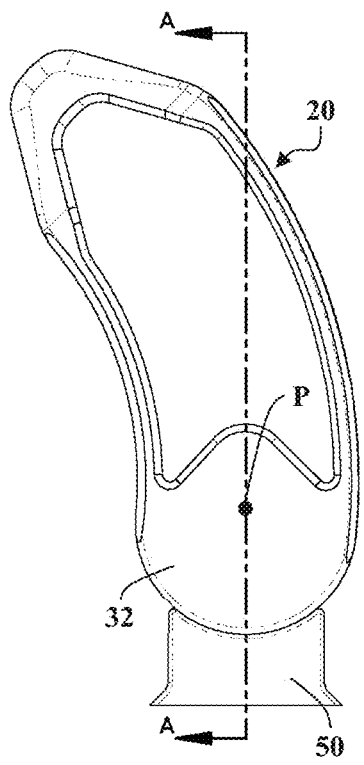
FIGS. 5A-5D are side views and cross-sectional views the intervertebral spacer of FIGS. 3A-3C.
Figure 5B:
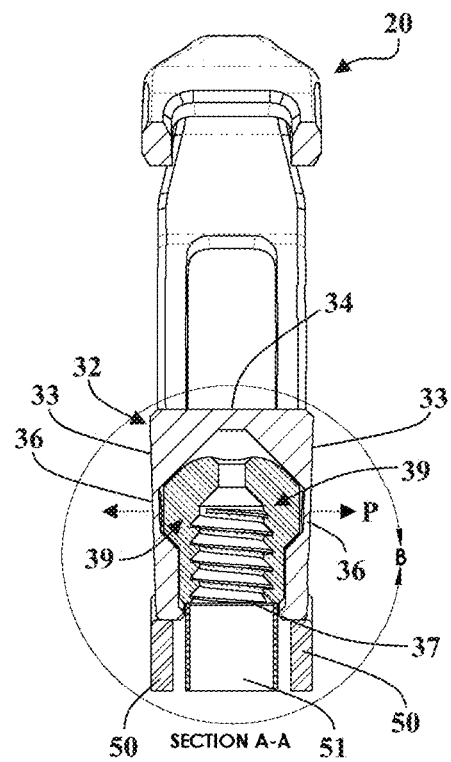

FIGS. 5A-5D are side views and cross-sectional views of the intervertebral spacer 20. Particularly, FIG. 5A is a side view of the intervertebral spacer 20 and identifies a vertical cross-section A-A which cuts through the intervertebral spacer 20 in a manner that is parallel with and coincides with a pivotal axis P of the articulating component 22. FIG. 5B is a cross-sectional view of the vertical cross-section A-A of the intervertebral spacer 20. As can be seen, the protrusions 39 of the articulating component 22 take the form of truncated cones which extend from the body of the articulating component 22 in the direction of and coinciding with the pivotal axis P. In alternative embodiments, the protrusions 39 take the form of blunted cones. Likewise, the indentations 36 in the proximal end portion 32 of the main body 21 are in the form of truncated conical recesses in the direction of and coinciding with the pivotal axis P. In alternative embodiments, the indentations 36 take the form of blunted conical recesses. As can be seen in the detail view of FIG. 6B, the truncated conical shape of the protrusions 39 of the articulating component 22 thus have a shape that closely coincides with the indentations 36 in the proximal end portion 32 of the main body 21. However, as best seen in the detail view of FIG. 6C, a small gap 42 is maintained between the upper/lower wall 33 and the articulating component 22. In this way, the articulating component 22 is held firmly in place in all directions within the opening 23 of the main body 21 with minimal movement of the articulating component 22 being possible, aside from the singular rotational degree of freedom about the pivotal axis P.

Figure 5C:
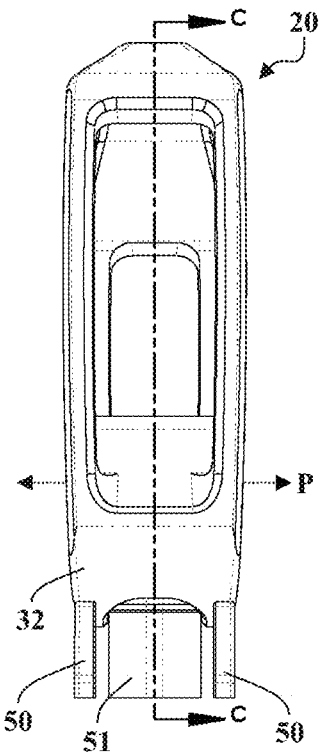
Figure 5D:
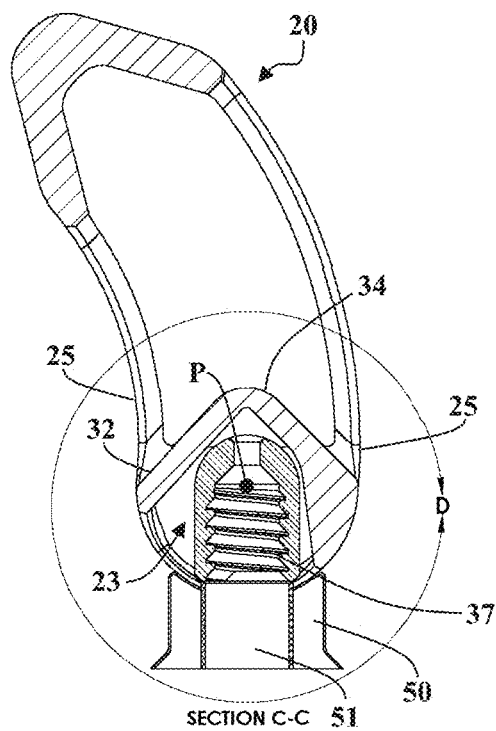
Figure 6A:
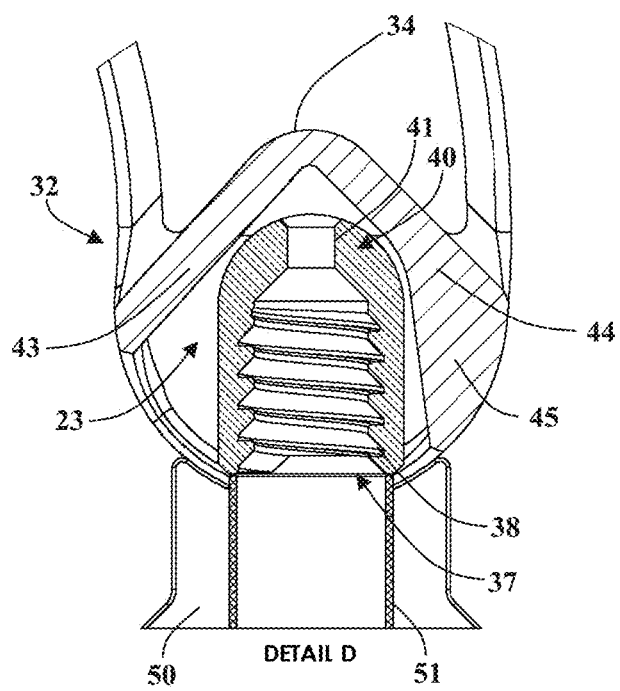
FIGS. 6A-6C are detailed views of the cross-sectional views of the intervertebral spacer of FIGS. 5B and 5D.
Figure 6B:
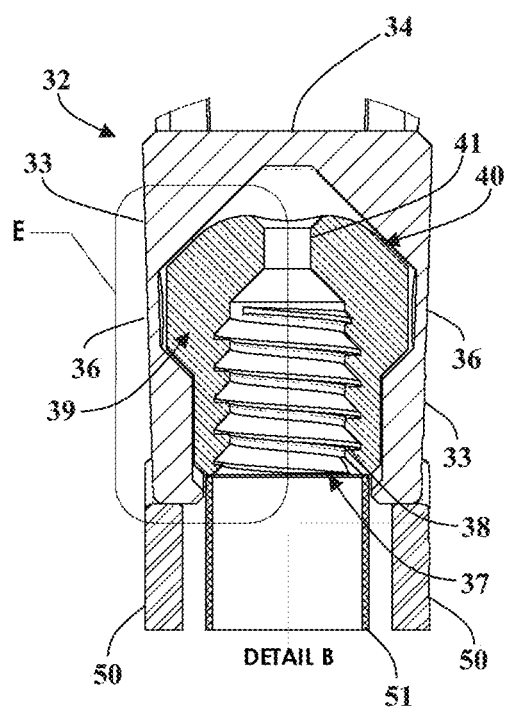
Figure 6C:
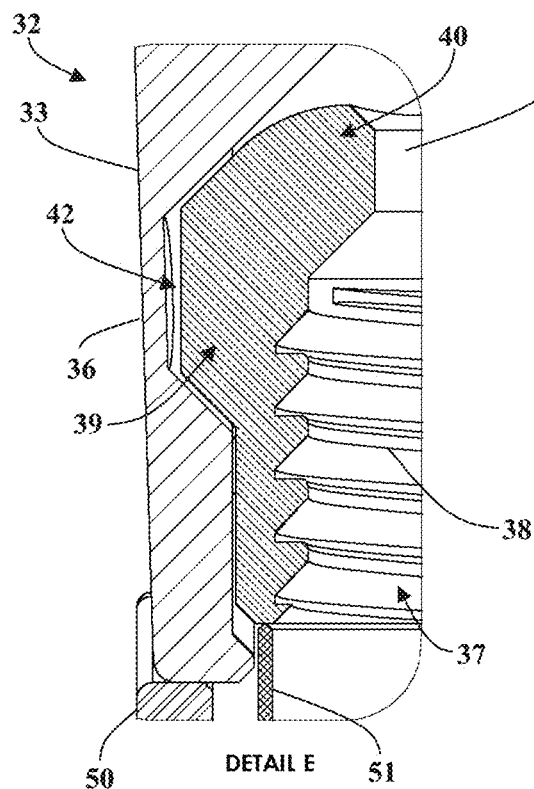

Similarly, FIG. 5C is a side view of the intervertebral spacer 20 and identifies a vertical cross-section C-C which cuts through the intervertebral spacer 20 in a manner that is perpendicular with a pivotal axis P of the articulating component 22. FIG. 5D is a cross-sectional view of the vertical cross-section C-C of the intervertebral spacer 20. As can be seen, the inner wall 34 and the side walls 25 are shaped to accommodate rotation of the articulating component 22 about the pivotal axis P within the opening 23. Additionally, the inner wall 34 and the side walls 25 are shaped to limit the range of motion of the articulating component 22 within the opening 23. In the illustrated example the inner wall 34 and the side walls 25 limit the range of motion of the articulating component 22 to about 55° of possible rotation about the pivotal axis P before being inhibited from further rotation. As best seen in the detail view of FIG. 6A, in order to delimit the range of motion of the articulating component 22, the inner wall 34 includes a limiting wall portions 43 and 44 that each have a surface facing the interior of the opening 23 that delimits the range of motion of the articulating component 22 by inhibiting its rotation about the pivotal axis P. The limiting wall portions 43 and 44 are joined together at an angle (about 90°, in the illustrated embodiment), which in part defines the total range of motion of the articulating component 22.

In some embodiments, such as the one illustrated, the inner wall 34 and/or the side walls 25 are configured to accommodate a greater amount of rotation in one direction than the other, relative to the vertical orientation of articulating component 22 in which the articulating component 22 is originally manufactured (i.e., the illustrated orientation of the articulating component 22). In one embodiment, the articulating component 22 can rotate further in a direction of the curvature of the main body 21 (to the left in the illustration of FIG. 6A). In the illustrated embodiment, starting from the vertical orientation of articulating component 22, the articulating component 22 can rotate about 45° in the direction of the curvature of the main body 21 (clockwise rotation, in the illustrated perspective) and about 10° in the opposite direction (counter-clockwise rotation). To this end, limiting wall portion 44, is has a flared end portion 45 (which is opposite the end that joins with the limiting wall portion 43) that further inhibits rotation of the articulating component 22 about the pivotal axis P in that direction (to the right in the illustration of FIG. 6A). Alternatively, the limiting wall portion 44 could similar have a bent end portion 45, to achieve the same result.

Finally, as can be seen in the FIGS. 5B and 5D, the longitudinal axis of the threaded bore 37 is perpendicular to a pivotal axis P of the articulating component 22. In this way, the singular rotational degree of freedom about the pivotal axis P enables adjustment of the interface angle between the main body 21 of the intervertebral spacer 20 and the insertion tool T. As discussed above with respect to FIGS. 1A-1D, this adjustment is useful to facilitate a transforaminal approach for implanting an intervertebral spacer, such as the intervertebral spacer 20.

Figure 7A:
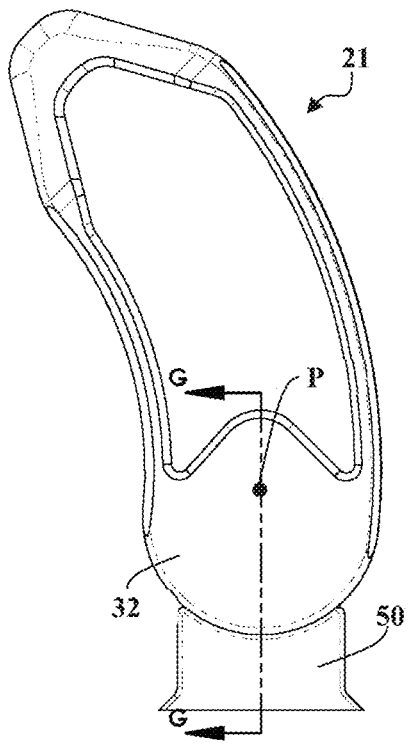
FIGS. 7A-7D are side views and cross-sectional views of a main body and an articulating component of the intervertebral spacer of FIGS. 3A-3C.
Figure 7B:
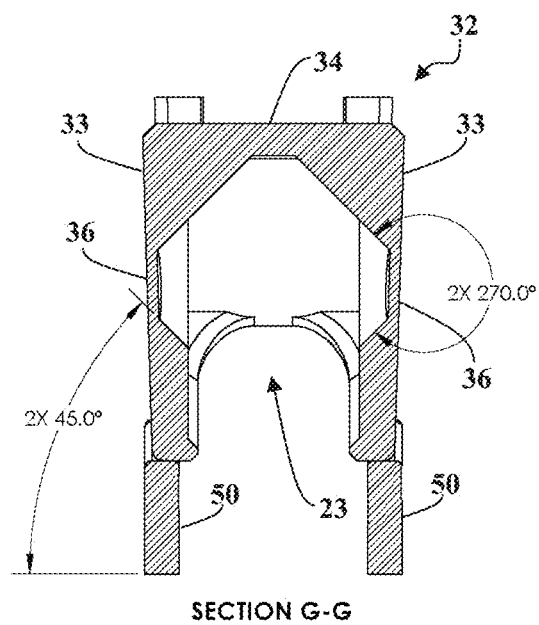

FIGS. 7A-7D are side views and cross-sectional views of the main body 21 and articulating component 22 of the intervertebral spacer 20. Particularly, FIG. 7A is a side view of the main body 21 and identifies a vertical cross-section G-G which cuts through the intervertebral spacer 20 in a manner that is parallel with and coincides with the pivotal axis P of the articulating component 22. FIG. 7B is a cross-sectional view of the vertical cross-section G-G of the intervertebral spacer 20. As mentioned above, in the exemplary illustrated embodiments, the indentations 36 in the proximal end portion 32 of the main body 21 are in the form of truncated conical recesses in the direction of and coinciding with the pivotal axis P. As can be seen, the conical shape of the indentations 36 extend into the upper and lower walls 33 at an angle of about 45°, relative to the interior surface of the upper and lower walls 33. The conical shape is truncated at about two-thirds of the thickness of the upper and lower walls 33.

Figure 7C:
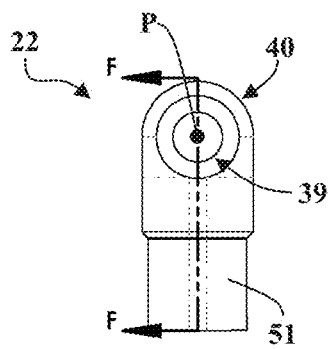
Figure 7D:
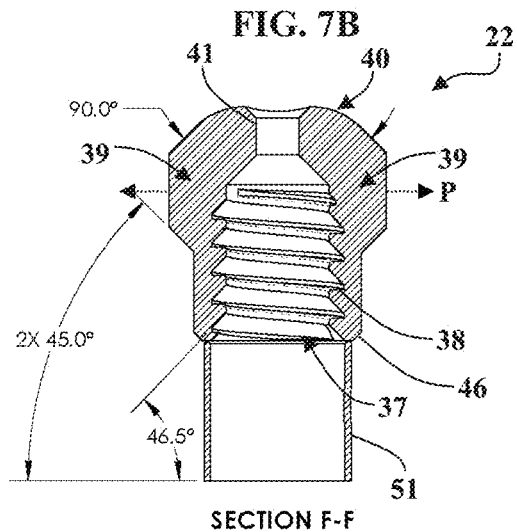
Figure 8A:
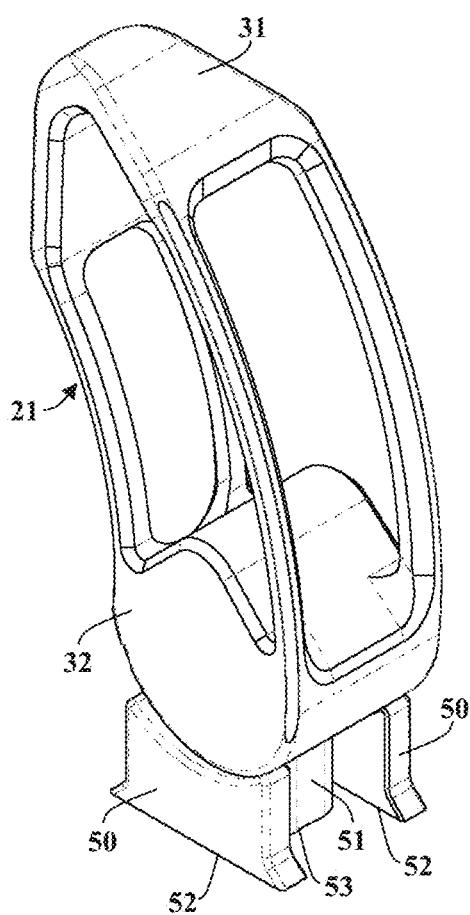
FIGS. 8A-8C are perspective views of an alternative intervertebral spacer having removable supports adapted for additive manufacture of the intervertebral spacer.
Figure 8B:
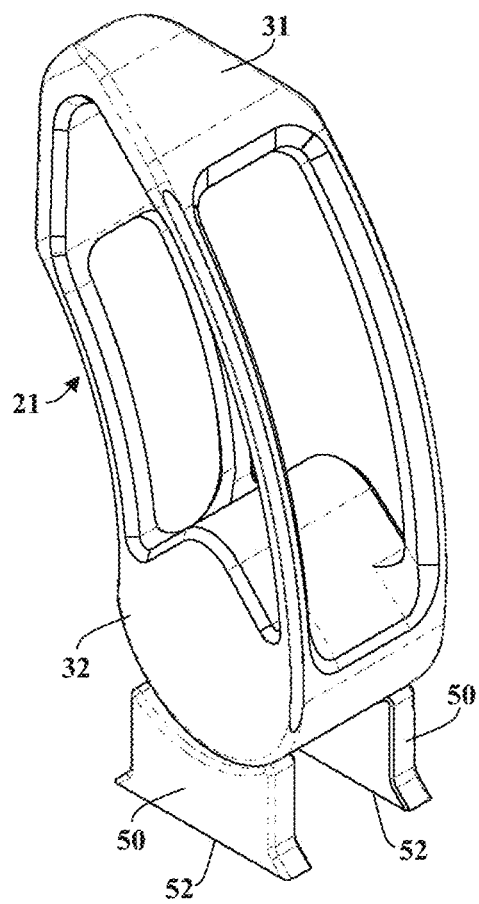
Figure 8C:
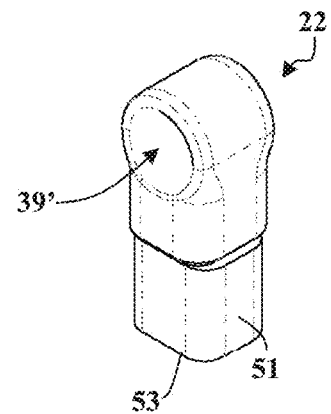
Figure 9C:
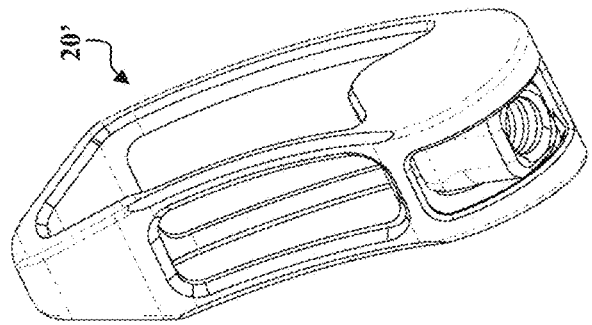
FIGS. 9A-9D are perspective views of the intervertebral spacer of FIGS. 8A-8C illustrating removal of the supports after manufacture.
Figure 9B:
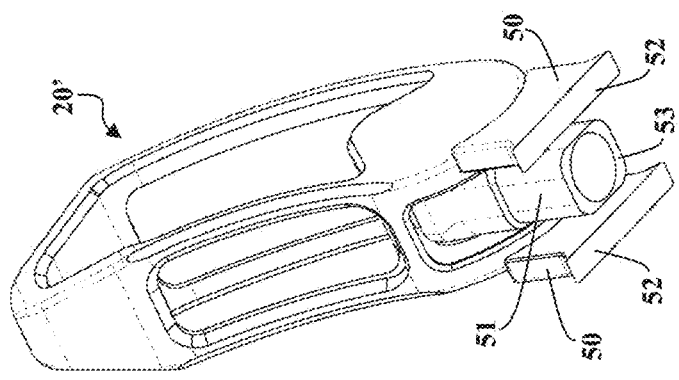
Figure 9D:
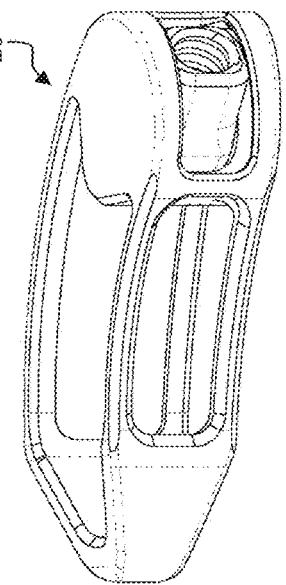
Figure 9A:
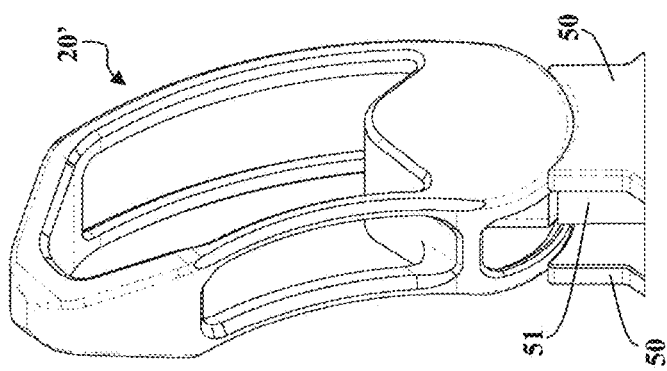

Similarly, FIG. 7C is a side view of the articulating component 22 and identifies a vertical cross-section F-F which cuts through the articulating component 22 in a manner that is parallel with and coincides with the pivotal axis P of the articulating component 22. FIG. 7D is a cross-sectional view of the vertical cross-section F-F of the intervertebral spacer 20. As mentioned above, the protrusions 39 of the articulating component 22 take to form of truncated cones which extend from the body of the articulating component 22 in the direction of and coinciding with the pivotal axis P. As can be seen, the conical shape of the protrusions 39 extend from the body of the articulating component 22 at an angle of about 45°, relative to the exterior surface of the articulating component 22. The conical shape of the protrusions 39 is truncated so as to match the truncated conical shape of the indentations 36 in the proximal end portion 32 of the main body 21.

As best seen in FIG. 7C, the truncated nose 40 has a rounded semi-circular form in a direction that is perpendicular to the pivotal axis P. However, as best seen in FIG. 7D, the truncated nose 40 has a truncated triangular form in a direction parallel with the pivotal axis P, having an angle of about 45°. Additionally, as can be seen in FIG. 7D, the central bore 41 extends from the threaded bore 37 through the tip of the truncated nose 40 so as to communicate the threaded bore 37 with the opening 23. Finally, a distal end of articulating component has a beveled edge 46. The surface of the beveled edge 46 has a normal vector at an angle of about 46.5°, relative to a normal vector to the rest of the exterior surface of the articulating component 22.

FIGS. 8-12 illustrate an intervertebral spacer 20', which is similar to the intervertebral spacer 20 except in the manner of engagement between the main body 21 and the articulating component 22 to provide rotation about the pivotal axis P. FIGS. 8-12 are essentially similar to FIGS. 3-7 and are not described in complete detail. In particular, FIGS. 3A-3C are essentially similar the FIGS. 8A-8C, FIGS. 4A-4D are essentially similar to FIGS. 9D-9D, FIGS. 5A-5D are essentially similar to FIGS. 10D-10D, FIGS. 6A-6D are essentially similar to FIGS. 11D-11D, and FIGS. 7A-7D are essentially similar to FIGS. 12D-12D. Moreover, like components are labeled with like reference numerals in the FIGS. 8-12.

Figure 10A:
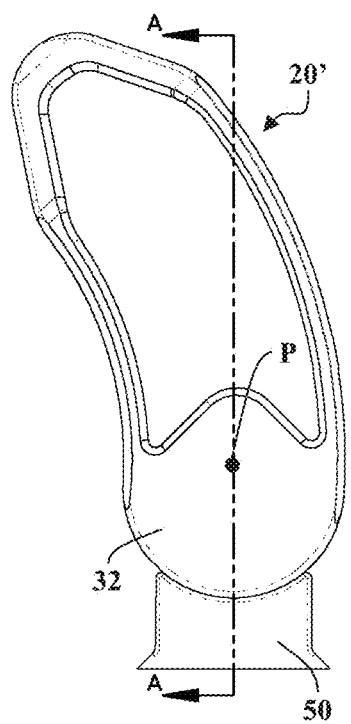
FIGS. 10A-10D are side views and cross-sectional views the intervertebral spacer of FIGS. 8A-8C.
Figure 10B:
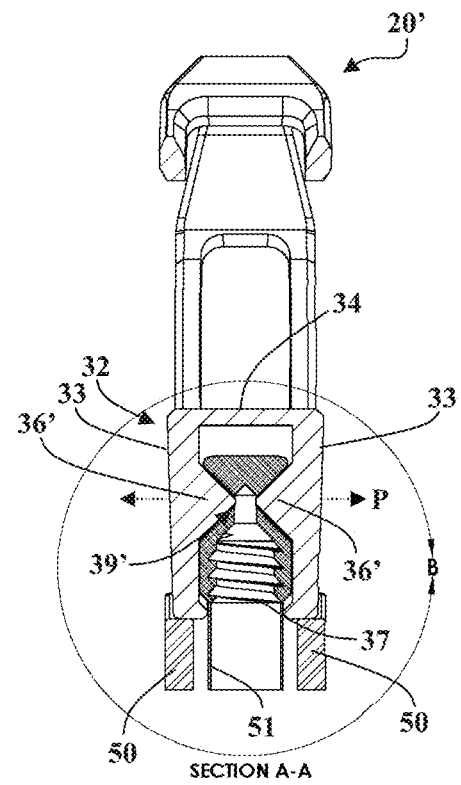
Figure 10C:
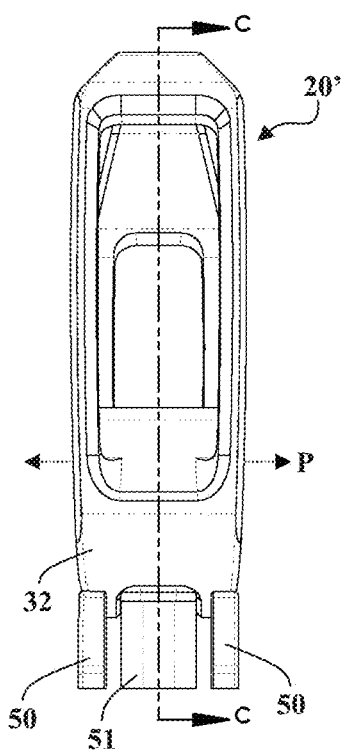
Figure 10D:
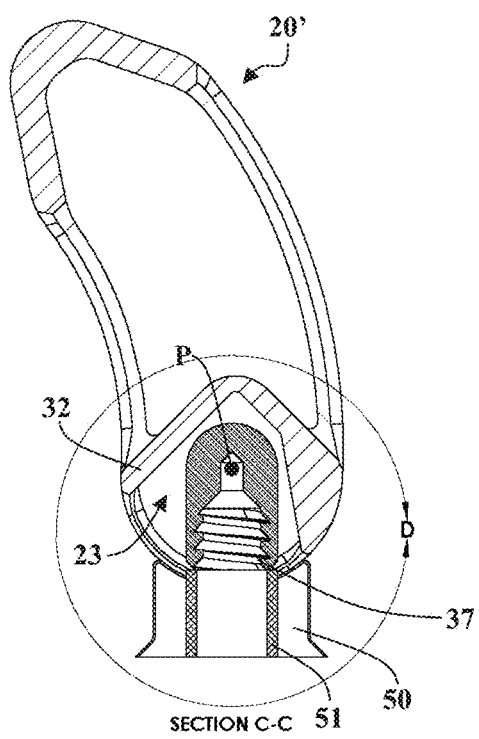
Figure 11A:
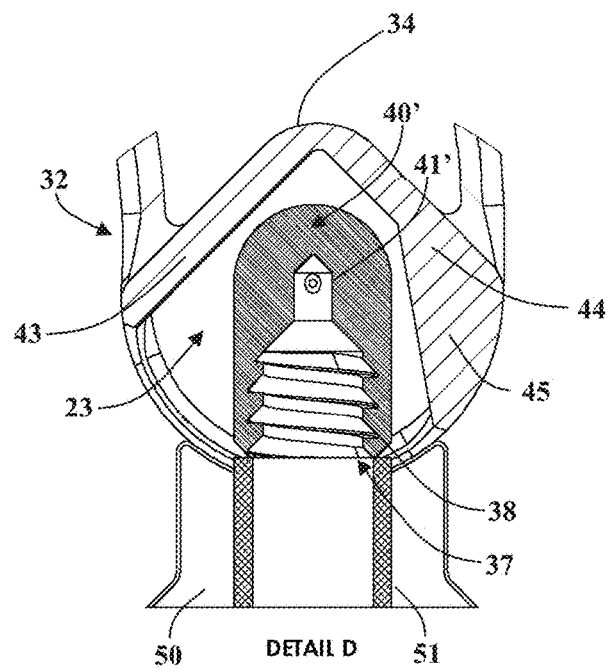
FIGS. 11A-11C are detailed views of the cross-sectional views of the intervertebral spacer of FIGS. 10B and 10D.
Figure 11B:
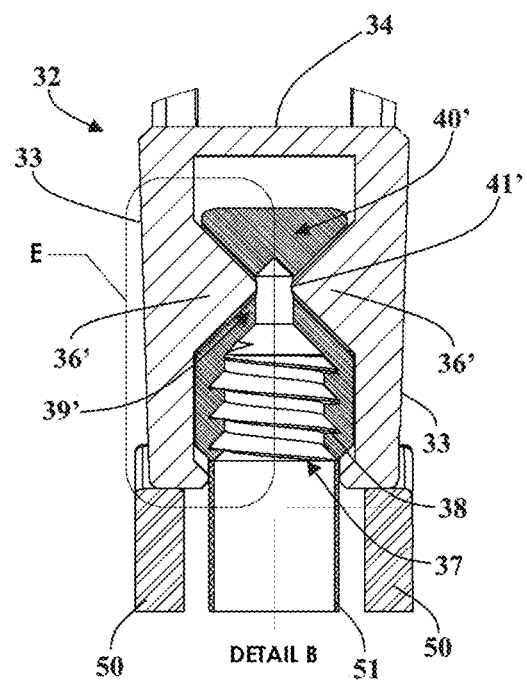
Figure 11C:
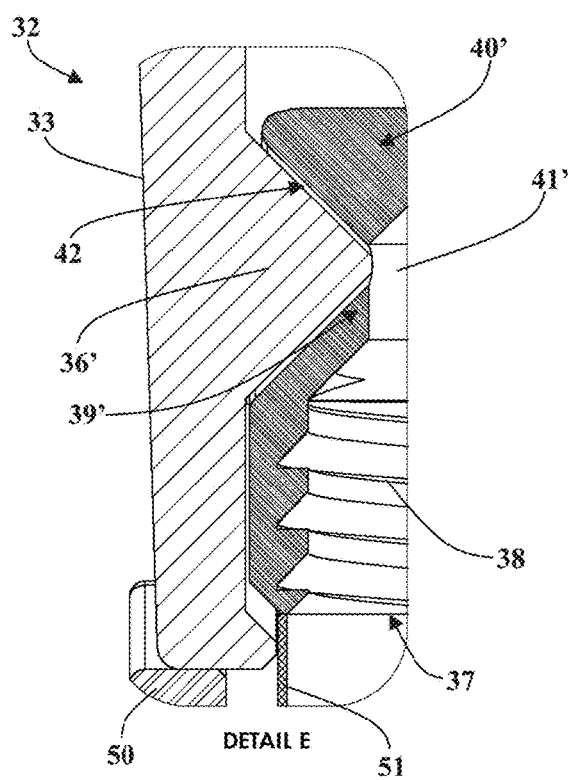

With reference to FIG. 10B, unlike the intervertebral spacer 20, the proximal end portion 32 of the intervertebral spacer 20' has protrusions 36' that take the form of cones which extend from the interior surface of the upper and lower walls 33 in the direction of and coinciding with the pivotal axis P. Similarly, the articulating component 22 has indentations 39' that are in the form of conical recesses in the direction of and coinciding with the pivotal axis P. As can be seen in the detail view of FIG. 11B, the conical shape of the protrusions 36' in the proximal end portion 32 of the main body 21 have a shape that closely engages with the indentations 39' of the articulating component 22. However, as best seen in the detail view of FIG. 11C, a small gap 42 is maintained between the upper/lower wall 33 and the articulating component 22. In this way, the articulating component 22 is held firmly in place within the opening 23 of the main body 21 with minimal movement of the articulating component 22 being possible, aside from the singular rotational degree of freedom about the pivotal axis P.

Figure 12A:
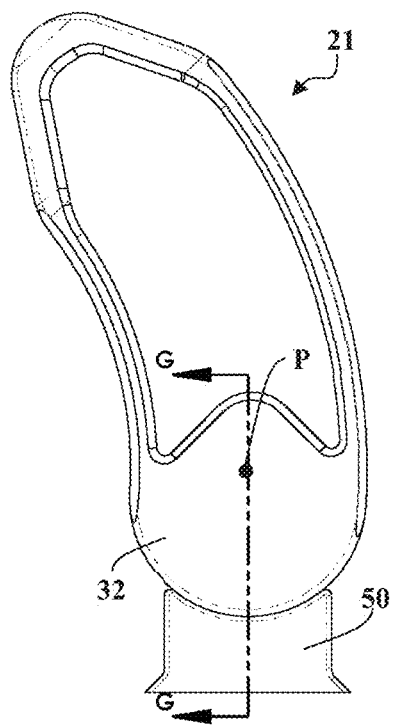
FIGS. 12A-12D are side views and cross-sectional views of a main body and an articulating component of the intervertebral spacer of FIGS. 8A-8C.
Figure 12B:
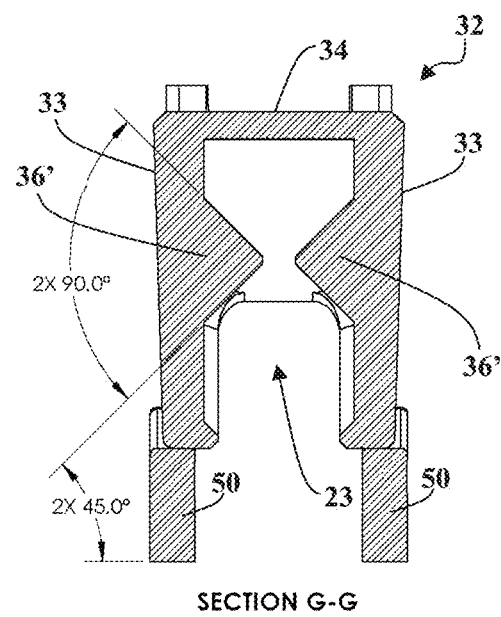

As best seen in FIG. 12B, the conical shape of each of the protrusions 36' extends from the interior surface of the upper and lower walls 33 at an angle of about 45°, relative to the interior surface of the upper and lower walls 33, and terminates at a point having a 90° angle. Likewise, as best seen in FIG. 12D, the conical shape of the indentations 39' extend into articulating component 22 at an angle of about 45°, relative to the exterior surface of the articulating component 22, and terminates at a point having a 90° angle.

Figure 12C:
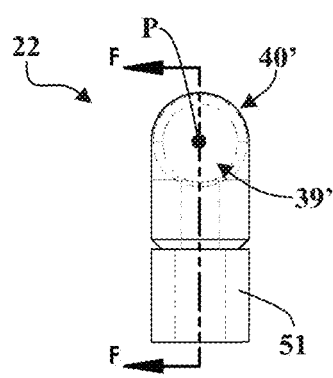
Figure 12D:
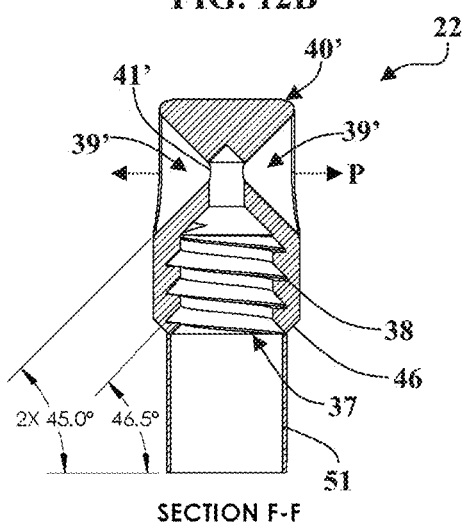

As best seen in FIG. 12C, the articulating component 22 the intervertebral spacer 20' has truncated nose 40' having a rounded form in a direction that is perpendicular to the pivotal axis P. However, as best seen in FIG. 12D the truncated nose 40' has a squared form in a direction parallel with the pivotal axis P. Additionally, as can be seen in FIG. 12D, the central bore 41' extends from the threaded bore 37, but is terminated in a conical point and does not extend completely through the truncated nose 40'.

In at least one embodiment, the spacer 20, 20' is manufactured using a digital additive manufacturing process and, in particular, using a three-dimensional object printer. It will be appreciated that digital additive manufacturing is a process of making a three-dimensional solid object of virtually any shape from a digital model by adding material. Three-dimensional object printing or "3D printing" is an additive process in which one or more ejector heads deposit material to incrementally build an object. Material is typically deposited in discrete quantities in a controlled manner to form layers that collectively form the object. The initial layer of material is deposited onto a substrate, and subsequent layers are deposited on top of previous layers. Three-dimensional object printing is distinguishable from traditional object-forming techniques, which mostly rely on the removal of material from a work piece by a subtractive process, such as cutting or drilling.

Figure 13:
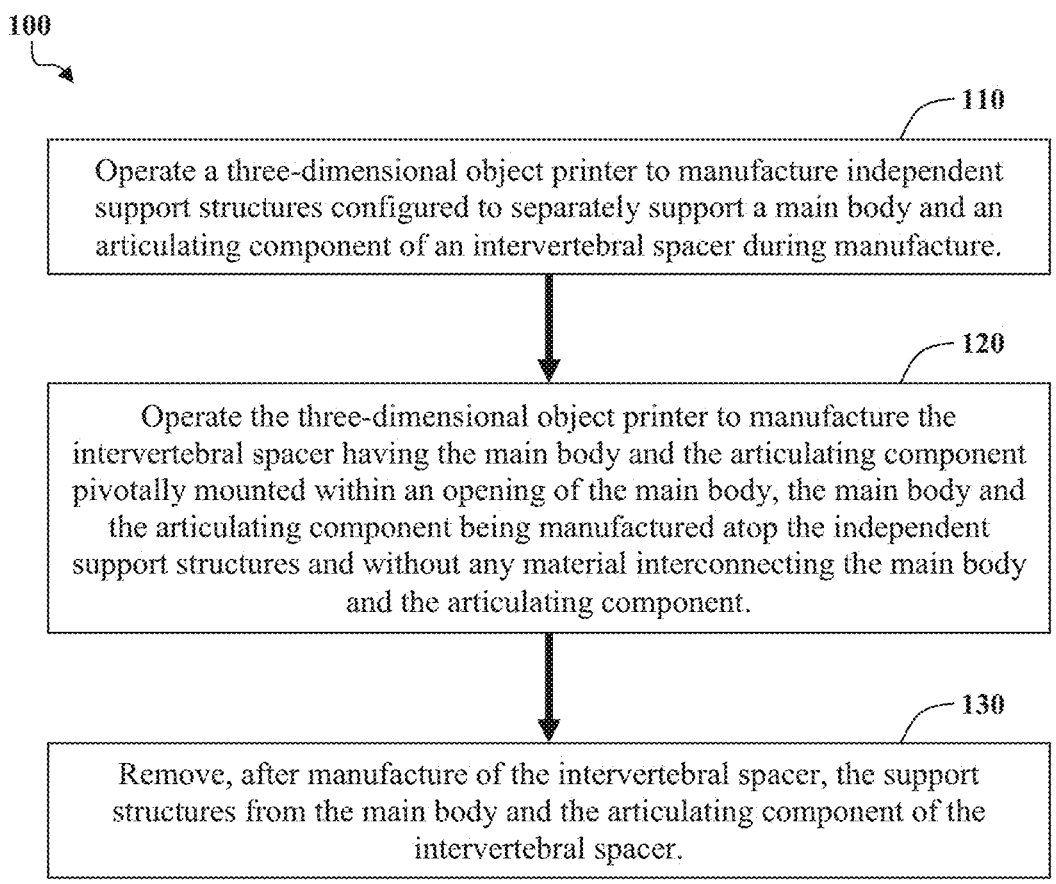
FIG. 13 is a logical flow diagram for a method of manufacturing an intervertebral spacer using a three-dimensional object printer or equivalent additive manufacturing process.

FIG. 13 is a logical flow diagram for a method 100 of manufacturing the intervertebral spacer 20, 20' using a three-dimensional object printer or equivalent additive manufacturing process. It will be appreciated by those of ordinary skill in the art that a three-dimensional object printer may, for example, comprise a platen, an ejector head, and a controller. The ejector head has one or more ejectors configured to eject drops of build material towards a surface of the platen to form a three-dimensional object. The ejector head is configured to move relative to the platen. Particularly, either the platen is moved via operation of actuators operatively connected to the platen or the ejector head is moved via operation of actuators operatively connected to the ejector heads, or both. The controller is operatively connected to the ejector head and the actuators and configured to operate the ejector head and the actuators with reference to image data, such as a 3D model, to form a three-dimensional object on the surface of the platen.

The method 100 begins with a step of operating a three-dimensional object printer to manufacture independent support structures configured to separately support a main body and an articulating component of an intervertebral spacer during manufacture (block 110). Particularly, a controller operates actuators to position ejectors of an ejector head above a platen and to eject build material onto the platen at different locations to form the support structures 50 and 51. Generally, the support structures 50 and 51 are built by forming one layer of build material after another in a sequential manner, where each layer is built atop the preceding layer. To form each layer of the support structures 50 and 51, the controller may, for example, operate the actuators of the printer to sweep the ejector head one or more times relative to the platen in a process direction, which is parallel to the platen, while ejecting drops of material onto the platen. After each layer is formed, the ejector head moves away from the platen in a vertical direction, which is perpendicular to the platen, to begin printing the next layer atop the previously formed layer.

The method 100 continues with a step of operating the three-dimensional object printer to manufacture the intervertebral spacer having the main body and the articulating component pivotally mounted within an opening of the main body, the main body and the articulating component being manufactured atop the independent support structures and without any material interconnecting the main body and the articulating component (block 120). Particularly, a controller operates actuators to position ejectors of an ejector head above a platen and to eject build material onto the platen at different locations to form the main body 21 of the intervertebral spacer 20 atop the support structures 50 and the articulating component 22 of the intervertebral spacer 20 atop the support structure 51. As with the support structures 50 and 51, the main body 21 and the articulating component 22 are built by forming one layer of build material after another in a sequential manner, where each layer is built atop the preceding layer.

As the main body 21 and the articulating component 22 are formed, they are independently supported by the supports 50 and 51. In particular, the proximal end 32 of the main body 21 is formed directly atop the supports 50 and the distal end of the articulating component 22 is formed directly atop the support 51. This is made possible by virtue of the vertical orientation of the intervertebral spacer 20, 20' during manufacture. Particularly, the upper and lower walls 34 of the proximal end 32 rest directly atop the two supports 50 with an orientation such that the opening 23 faces the support 51 (which is situated between the two supports 50). This enables the articulating component 22 to be formed within the opening 23 simultaneously with the formation of the proximal end 32 of the main body 21. Thus, the main body 21 and the articulating component 22 can be built with the small gap 42 situated therebetween, as described above with respect to FIGS. 6B-6C or FIGS. 11B-11C. Moreover, there is advantageously no need for any frangible support material between the articulating component 22 and the main body 21 to hold the articulating component 22 within the opening 23 during manufacture.

The method 100 concludes with removing, after manufacture of the intervertebral spacer, the support structures from the main body and the articulating component of the intervertebral spacer (block 130). Particularly, after the additive manufacturing process is complete, the supports 50 and 51 are removed, leaving the finished intervertebral spacer 20, as shown in FIGS. 4C-4D or FIGS. 9C-9D. The supports 50 and 51 can be configured to be frangible so as to be easily snapped off from the articulating component 22 and the main body 21. In that regard, a line of weakness or thinner material can be formed between the support and the component being supported so that the supports can still provide vertical support for the component during manufacture, but can be readily snapped off by a lateral force. Alternatively, the build supports can be removed in a machining operation, such as cutting. It can be appreciated that the supports can be removed at any time after manufacture and before the intervertebral spacer 20, 20' is introduced into a patient.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of manufacturing an intervertebral spacer, the method comprising:
   manufacturing, using an additive manufacturing process, atop a surface, at least one first support structure configured to support a main body of the intervertebral spacer during manufacture and at least one second support structure configured to support an articulating component of the intervertebral spacer during manufacture;
   manufacturing, using the additive manufacturing process, the main body atop the at least one first support structure, the main body having a distal end and a proximal end that are connected by side walls that are spaced apart from one another so as to define an interior cavity therebetween, the proximal end having a first proximal end wall and a second proximal end wall, a proximal end opening being defined between the first proximal end wall and the second proximal end wall;
   manufacturing, using the additive manufacturing process, the articulating component atop the at least one second support structure without any material interconnecting the main body and the articulating component, the articulating component being pivotally mounted within the proximal end opening and configured to interconnect with a tool for inserting the intervertebral spacer; and
   removing, after the manufacture of the main body and the articulating component, the at least one first support structure from the main body and the at least one second support structure from the articulating component.

2. The method according to claim 1, the manufacturing of the main body further comprising:
   manufacturing the proximal end of the main body directly atop the at least one first support structure.

3. The method according to claim 2, the manufacturing of the main body further comprising:
   manufacturing the first proximal end wall directly atop a first portion of the at least one first support structure; and
   manufacturing the second proximal end wall directly atop a second portion of the at least one first support structure.

4. The method according to claim 3, the manufacturing of the at least one second support structure further comprising:
   manufacturing the at least one second support structure situated between the first portion of the at least one first support structure and the second portion of the at least one first support structure.

5. The method according to claim 2, the manufacturing of the main body further comprising:
   manufacturing the proximal end of the main body directly atop the at least one first support structure oriented such that the proximal end opening of the proximal end faces the at least one second support structure.

6. The method according to claim 2, the manufacturing of the articulating component further comprising:
   manufacturing the articulating component within the proximal end opening simultaneously with the manufacturing of the proximal end of the main body.

7. The method according to claim 1, the manufacturing of the articulating component further comprising:
   manufacturing the articulating component within the proximal end opening with a gap defined between the articulating component and the proximal end of the main body.

8. The method according to claim 1, the manufacturing of the articulating component further comprising:
   manufacturing a distal end of the articulating component directly atop the at least one second support structure.

9. The method according to claim 8, the manufacturing of the articulating component further comprising:
   manufacturing the articulating component directly atop the at least one second support structure oriented such that a central bore in the distal end of the articulating component faces in a direction of the at least one second support structure, the central bore being configured to interconnect with the tool.

10. The method according claim 1, the removing further comprising:
    applying lateral forces to break the at least one first support structure from the main body; and
    applying lateral forces to break the at least one second support structure from the articulating component.

11. The method according to claim 1, the removing further comprising:
    cutting, with a machine, the at least one first support structure from the main body; and
    cutting, with the machine, the at least one second support structure from the articulating component.

12. The method according to claim 1, the additive manufacturing process comprising:
    operating a three-dimensional object printer to eject build material toward the surface.

13. The method according to claim 12, the operating the three-dimensional object printer further comprising:
    ejecting the build material to form layers of build material, one after another in a sequential manner.

* * * * *